(12) United States Patent
Bacon

(10) Patent No.: US 8,329,271 B2
(45) Date of Patent: Dec. 11, 2012

(54) MEDICAMENT CONTAINER

(75) Inventor: Raymond Bacon, Hampshire (GB)

(73) Assignee: Clinical Designs Limited, Cambridge (GB)

( * ) Notice: Subject to any disclaimer, the term of this patent is extended or adjusted under 35 U.S.C. 154(b) by 559 days.

(21) Appl. No.: 11/792,722

(22) PCT Filed: Dec. 14, 2005

(86) PCT No.: PCT/GB2005/004834
§ 371 (c)(1),
(2), (4) Date: Jun. 11, 2007

(87) PCT Pub. No.: WO2006/067383
PCT Pub. Date: Jun. 29, 2006

(65) Prior Publication Data
US 2008/0107848 A1 May 8, 2008

(30) Foreign Application Priority Data
Dec. 23, 2004 (GB) .................................. 0428204.2

(51) Int. Cl.
B29D 22/00 (2006.01)
A61M 11/00 (2006.01)
H05B 6/00 (2006.01)
B29C 45/00 (2006.01)

(52) U.S. Cl. .................. 428/35.7; 128/200.23; 264/454; 264/478; 264/513

(58) Field of Classification Search .................. 428/35.7; 128/200.23; 264/454, 478, 513
See application file for complete search history.

(56) References Cited

U.S. PATENT DOCUMENTS

| 2,002,835 A | 5/1935 | Rose |
| 2,716,013 A | 8/1955 | Tinker |
| 2,922,613 A | 6/1960 | Beecham |
| 3,103,335 A | 9/1963 | Martinez |

(Continued)

FOREIGN PATENT DOCUMENTS

AU 776816 7/2002

(Continued)

OTHER PUBLICATIONS

Definition of "mouth"; http://www.merriam-webster.com/dictionary/mouth; 2011.*
Machine Translation of Claim 1 of DE 1077932 (Date Unavailable).*
Machine Translation of Claim 1 of DE 202004021188 U (Date Unavailable).*
Machine Translation of Claim 1 of DE 629163 (Date Unavailable).*
Machine Translation of Claim 1 of DE 8715223 U (Date Unavailable).*

(Continued)

Primary Examiner — Rena Dye
Assistant Examiner — James Yager
(74) Attorney, Agent, or Firm — Nixon & Vanderhye P.C.

(57) ABSTRACT

A medicament source has a container and a crimped closure. The closure sealingly holds to the container a metered-dose release valve, of which the spout only is visible externally. The container has a neck and a protruding rim at which the crimp locates. The container is of molded polymer and has an outer, perforate sleeve of aluminum, providing mechanical strength for pressure retention. The neck has a relatively thicker wall thickness and the end is domed inwards, both for pressure retention. The polymer is of three layers or laminations. The innermost layer is of polytetrafluoroethylene (PTFE) material to provide an inert layer with which the medicament and its propellant will not react or combine in any way. The middle polymer layer is of nylon material to provide a propellant tight layer, to contain the propellant, whose molecules may be able to pass through the PTFE layer. The outer polymer layer is of polypropylene (PP) to provide both water tightness and mechanical integrity of the container.

14 Claims, 3 Drawing Sheets

U.S. PATENT DOCUMENTS

| | | |
|---|---|---|
| 3,190,497 A | 6/1965 | Anthon |
| 3,329,389 A | 7/1967 | Clark |
| 3,598,288 A | 8/1971 | Posgate |
| 3,746,196 A | 7/1973 | Sako |
| 4,142,651 A | 3/1979 | Leopoldi |
| 4,361,148 A | 11/1982 | Shackleford |
| 4,370,368 A | 1/1983 | Hirata et al. |
| 4,393,106 A | 7/1983 | Maruhashi et al. |
| 4,486,378 A | 12/1984 | Hirata et al. |
| 4,576,157 A | 3/1986 | Raghuprasad |
| 4,664,107 A | 5/1987 | Wass |
| 4,753,371 A | 6/1988 | Michielin |
| 4,817,822 A | 4/1989 | Rand |
| 4,955,371 A | 9/1990 | Zamba |
| 4,984,158 A | 1/1991 | Hillsman |
| 5,020,527 A | 6/1991 | Dessertine |
| 5,031,610 A | 7/1991 | Armstrong |
| 5,042,685 A | 8/1991 | Moulding, Jr. |
| 5,049,345 A * | 9/1991 | Collette et al. ............... 264/255 |
| 5,069,204 A | 12/1991 | Smith |
| 5,119,806 A | 6/1992 | Palson |
| 5,152,456 A | 10/1992 | Ross |
| 5,184,761 A | 2/1993 | Lee |
| 5,193,745 A | 3/1993 | Holm |
| 5,217,004 A | 6/1993 | Blasnik |
| 5,239,992 A | 8/1993 | Bougamont |
| 5,261,601 A | 11/1993 | Ross |
| 5,273,172 A | 12/1993 | Rossbach |
| 5,295,479 A | 3/1994 | Lankinen |
| 5,299,701 A | 4/1994 | Barker |
| 5,347,998 A | 9/1994 | Hodson |
| 5,388,572 A | 2/1995 | Mulhauser |
| 5,408,994 A | 4/1995 | Wass |
| 5,415,161 A | 5/1995 | Ryder |
| 5,421,482 A | 6/1995 | Garby |
| 5,482,030 A | 1/1996 | Klein |
| 5,487,378 A | 1/1996 | Robertson |
| 5,501,375 A | 3/1996 | Nilson |
| 5,511,540 A | 4/1996 | Bryant |
| 5,544,647 A | 8/1996 | Jewett |
| 5,544,657 A | 8/1996 | Kurowski |
| 5,546,932 A | 8/1996 | Galli |
| 5,549,101 A | 8/1996 | Trofast |
| 5,549,226 A | 8/1996 | Kopp |
| 5,564,414 A | 10/1996 | Walker |
| 5,611,444 A | 3/1997 | Garby |
| 5,622,163 A | 4/1997 | Jewett |
| 5,623,920 A | 4/1997 | Bryant |
| 5,645,050 A | 7/1997 | Zierenberg |
| 5,682,875 A | 11/1997 | Blower |
| 5,692,492 A | 12/1997 | Bruna |
| 5,718,355 A | 2/1998 | Garby |
| 5,772,085 A | 6/1998 | Bryant |
| 5,794,612 A | 8/1998 | Wachter |
| 5,809,997 A | 9/1998 | Wolf |
| 5,839,429 A | 11/1998 | Marnfeldt |
| 5,878,917 A | 3/1999 | Reinhard |
| 5,960,609 A | 10/1999 | Abrams |
| 5,988,496 A | 11/1999 | Bruna |
| 5,996,577 A | 12/1999 | Ohki |
| 6,014,970 A | 1/2000 | Ivri |
| 6,085,742 A | 7/2000 | Wachter |
| 6,142,146 A | 11/2000 | Abrams |
| 6,148,815 A | 11/2000 | Wolf |
| 6,149,054 A | 11/2000 | Cirrillo |
| 6,152,130 A | 11/2000 | Abrams |
| 6,164,494 A | 12/2000 | Marelli |
| 6,196,218 B1 | 3/2001 | Voges |
| 6,202,642 B1 | 3/2001 | McKinnon |
| 6,234,168 B1 | 5/2001 | Bruna |
| 6,240,918 B1 | 6/2001 | Ambrosio |
| 6,253,762 B1 | 7/2001 | Britto |
| 6,260,549 B1 | 7/2001 | Sosiak |
| 6,283,365 B1 | 9/2001 | Bason |
| 6,318,361 B1 | 11/2001 | Sosiak |
| 6,325,062 B1 | 12/2001 | Sosiak |
| 6,336,453 B1 | 1/2002 | Scarrott |
| 6,354,290 B1 | 3/2002 | Howlett |
| 6,357,442 B1 | 3/2002 | Casper |
| 6,360,739 B1 | 3/2002 | Rand |
| 6,397,839 B1 | 6/2002 | Stradella |
| 6,405,727 B1 | 6/2002 | MacMichael |
| 6,415,784 B1 | 7/2002 | Christrup |
| 6,422,234 B1 | 7/2002 | Bacon |
| 6,425,392 B1 | 7/2002 | Sosiak |
| 6,427,683 B1 | 8/2002 | Drachmann |
| 6,431,168 B1 | 8/2002 | Rand |
| 6,435,372 B1 | 8/2002 | Blacker |
| 6,439,227 B1 | 8/2002 | Myrman |
| 6,443,146 B1 | 9/2002 | Voges |
| 6,446,627 B1 | 9/2002 | Bowman |
| 6,460,537 B1 | 10/2002 | Bryant |
| 6,470,884 B2 | 10/2002 | Horlin |
| 6,474,331 B1 | 11/2002 | Rand |
| 6,510,847 B1 | 1/2003 | Helgesson |
| 6,516,799 B1 | 2/2003 | Greenwood |
| 6,546,928 B1 | 4/2003 | Ashurst |
| 6,553,988 B1 | 4/2003 | Holroyd |
| 6,581,590 B1 | 6/2003 | Genova |
| 6,596,260 B1 | 7/2003 | Brugger |
| 6,601,582 B2 | 8/2003 | Rand |
| 6,615,827 B2 | 9/2003 | Greenwood |
| 6,655,371 B2 | 12/2003 | Gallops |
| 6,655,379 B2 | 12/2003 | Clark |
| 6,659,307 B1 | 12/2003 | Stradella |
| 6,672,304 B1 | 1/2004 | Casper |
| 6,729,330 B2 | 5/2004 | Scarrott |
| 6,745,761 B2 | 6/2004 | Christrup |
| 6,752,145 B1 | 6/2004 | Bonney |
| 6,752,153 B1 | 6/2004 | Eckert |
| 6,755,190 B2 | 6/2004 | Rasmussen |
| 6,759,108 B1 | 7/2004 | Ota |
| 6,766,220 B2 | 7/2004 | McRae |
| 6,805,116 B2 | 10/2004 | Hodson |
| 6,823,863 B2 | 11/2004 | Huxham et al. |
| 6,860,262 B2 | 3/2005 | Christrup |
| 6,866,037 B1 | 3/2005 | Aslin |
| 6,866,038 B2 | 3/2005 | Bacon |
| 6,889,687 B1 | 5/2005 | Olsson |
| 6,907,876 B1 | 6/2005 | Clark |
| 6,926,002 B2 | 8/2005 | Scarrott |
| 7,007,689 B2 | 3/2006 | Burns |
| 7,036,505 B2 | 5/2006 | Bacon |
| 7,047,964 B2 | 5/2006 | Bacon |
| 7,047,967 B2 | 5/2006 | Knudsen |
| 7,072,738 B2 | 7/2006 | Bonney |
| 7,093,594 B2 | 8/2006 | Harrison |
| 7,100,530 B2 | 9/2006 | Lu |
| 7,107,986 B2 | 9/2006 | Rand |
| 7,147,170 B2 | 12/2006 | Nguyen |
| 7,167,776 B2 | 1/2007 | Maharajh |
| 7,191,918 B2 | 3/2007 | Ouyang |
| 7,195,134 B2 | 3/2007 | Ouyang |
| 7,219,664 B2 | 5/2007 | Ruckdeschel |
| 7,225,805 B2 | 6/2007 | Bacon |
| 7,234,460 B2 | 6/2007 | Greenleaf |
| 7,237,727 B2 | 7/2007 | Wang |
| 7,270,124 B2 | 9/2007 | Rasmussen |
| 7,275,660 B2 | 10/2007 | Stradella |
| 7,296,567 B2 | 11/2007 | Mahon |
| 7,299,800 B2 | 11/2007 | Stradella |
| 7,299,801 B2 | 11/2007 | Hodson |
| 7,306,116 B2 | 12/2007 | Fuchs |
| 7,318,434 B2 | 1/2008 | Gumaste |
| 7,322,352 B2 | 1/2008 | Minshull |
| 7,331,340 B2 | 2/2008 | Barney |
| 7,334,577 B2 | 2/2008 | Gumaste |
| 7,341,057 B2 | 3/2008 | Scarrott |
| 7,347,200 B2 | 3/2008 | Jones |
| 7,347,202 B2 | 3/2008 | Aslin |
| 7,367,333 B2 | 5/2008 | Hodson |
| 7,387,121 B2 | 6/2008 | Harvey |
| 7,400,940 B2 | 7/2008 | McRae |
| 7,418,961 B2 | 9/2008 | Jones |
| 7,448,342 B2 | 11/2008 | von Schuckmann |
| 7,454,267 B2 | 11/2008 | Bonney |
| 7,497,214 B2 | 3/2009 | Hodson |

| | | |
|---|---|---|
| 7,510,100 B2 | 3/2009 | Stradella |
| 7,597,099 B2 | 10/2009 | Jones |
| 7,637,260 B2 | 12/2009 | Holroyd |
| 7,743,765 B2 | 6/2010 | Hodson |
| 2001/0013342 A1 | 8/2001 | Burns |
| 2001/0013343 A1 | 8/2001 | Andersson |
| 2001/0025639 A1 | 10/2001 | Christrup |
| 2001/0032644 A1 | 10/2001 | Hodson |
| 2002/0000225 A1 | 1/2002 | Schuler |
| 2002/0011247 A1 | 1/2002 | Ivri |
| 2002/0026938 A1 | 3/2002 | Hodson |
| 2002/0043262 A1* | 4/2002 | Langford et al. ........ 128/200.23 |
| 2002/0088458 A1 | 7/2002 | Christrup |
| 2002/0100473 A1 | 8/2002 | Christrup |
| 2002/0104530 A1 | 8/2002 | Ivri |
| 2002/0104532 A1 | 8/2002 | Christrup |
| 2002/0139812 A1 | 10/2002 | Scarrott |
| 2002/0189611 A1 | 12/2002 | Greenwood |
| 2003/0033055 A1 | 2/2003 | McRae |
| 2003/0065149 A1* | 4/2003 | McGinnis et al. ........... 530/385 |
| 2003/0089368 A1 | 5/2003 | Zhao |
| 2003/0106550 A1 | 6/2003 | Harvey |
| 2003/0116155 A1 | 6/2003 | Rasmussen |
| 2003/0136401 A1 | 7/2003 | Jansen |
| 2003/0138559 A1 | 7/2003 | Ashurst |
| 2003/0150448 A1 | 8/2003 | Bacon |
| 2003/0178021 A1 | 9/2003 | Rasmussen |
| 2003/0183225 A1 | 10/2003 | Knudsen |
| 2003/0183226 A1 | 10/2003 | Brand et al. |
| 2003/0192535 A1 | 10/2003 | Christrup |
| 2003/0207057 A1 | 11/2003 | Britto |
| 2003/0230305 A1 | 12/2003 | Christrup |
| 2004/0005475 A1 | 1/2004 | Curie |
| 2004/0020486 A1 | 2/2004 | Huxham et al. |
| 2004/0025867 A1 | 2/2004 | Holroyd |
| 2004/0025868 A1 | 2/2004 | Bruna |
| 2004/0025870 A1 | 2/2004 | Harrison |
| 2004/0055596 A1 | 3/2004 | Bacon |
| 2004/0065320 A1 | 4/2004 | Bacon |
| 2004/0065326 A1 | 4/2004 | MacMichael et al. |
| 2004/0068218 A1* | 4/2004 | Davis et al. ........................ 604/2 |
| 2004/0069301 A1 | 4/2004 | Bacon |
| 2004/0079362 A1 | 4/2004 | Christrup |
| 2004/0089299 A1 | 5/2004 | Bonney |
| 2004/0107962 A1 | 6/2004 | Harrison |
| 2004/0129793 A1 | 7/2004 | Nguyen |
| 2004/0134488 A1 | 7/2004 | Davies |
| 2004/0134489 A1 | 7/2004 | Burns |
| 2004/0134824 A1* | 7/2004 | Chan et al. ................. 206/524.1 |
| 2004/0139965 A1 | 7/2004 | Greenleaf |
| 2004/0139966 A1 | 7/2004 | Hodson |
| 2004/0144798 A1 | 7/2004 | Ouyang |
| 2004/0149772 A1 | 8/2004 | Ouyang |
| 2004/0149773 A1 | 8/2004 | Ouyang |
| 2004/0172162 A1 | 9/2004 | Bonney |
| 2004/0187865 A1 | 9/2004 | Ashurst |
| 2004/0230286 A1* | 11/2004 | Moore et al. ................. 623/1.11 |
| 2005/0016528 A1 | 1/2005 | Aslin |
| 2005/0076904 A1 | 4/2005 | Jones |
| 2005/0081846 A1 | 4/2005 | Barney |
| 2005/0087191 A1 | 4/2005 | Morton |
| 2005/0121024 A1 | 6/2005 | Langford |
| 2005/0126469 A1 | 6/2005 | Lu |
| 2005/0143866 A1 | 6/2005 | McRae |
| 2005/0183724 A1 | 8/2005 | Gumaste |
| 2005/0205512 A1 | 9/2005 | Scarrott |
| 2005/0209558 A1 | 9/2005 | Marx |
| 2005/0263612 A1 | 12/2005 | Wang |
| 2006/0011197 A1 | 1/2006 | Hodson |
| 2006/0037611 A1 | 2/2006 | Mahon |
| 2006/0047368 A1 | 3/2006 | Maharajh |
| 2006/0060192 A1 | 3/2006 | Lu |
| 2006/0071027 A1 | 4/2006 | Davies |
| 2006/0131346 A1 | 6/2006 | Purkins |
| 2006/0151524 A1 | 7/2006 | Stradella |
| 2006/0163275 A1 | 7/2006 | Stradella |
| 2006/0174869 A1 | 8/2006 | Gumaste |
| 2006/0186223 A1 | 8/2006 | Wang |
| 2006/0213505 A1 | 9/2006 | Hodson |
| 2006/0213506 A1 | 9/2006 | Hodson |
| 2006/0213510 A1 | 9/2006 | Hodson |
| 2006/0231093 A1 | 10/2006 | Burge |
| 2006/0237002 A1 | 10/2006 | Bonney |
| 2006/0237009 A1 | 10/2006 | Jones |
| 2006/0243275 A1 | 11/2006 | Ruckdeschel |
| 2006/0254581 A1 | 11/2006 | Genova |
| 2006/0278225 A1 | 12/2006 | MacMichael et al. |
| 2006/0283444 A1 | 12/2006 | Jones |
| 2006/0289005 A1 | 12/2006 | Jones |
| 2006/0289008 A1 | 12/2006 | Rand |
| 2007/0017511 A1 | 1/2007 | Ohki |
| 2007/0029341 A1 | 2/2007 | Stradella |
| 2007/0051745 A1 | 3/2007 | Poulard |
| 2007/0056502 A1 | 3/2007 | Lu |
| 2007/0056580 A1 | 3/2007 | Jones |
| 2007/0056585 A1 | 3/2007 | Davies |
| 2007/0062518 A1 | 3/2007 | Geser et al. |
| 2007/0062522 A1 | 3/2007 | Bacon |
| 2007/0089735 A1 | 4/2007 | Langford |
| 2007/0119450 A1 | 5/2007 | Wharton |
| 2007/0144514 A1 | 6/2007 | Yeates |
| 2007/0163576 A1 | 7/2007 | Bacon |
| 2007/0181120 A1 | 8/2007 | Wright |
| 2007/0181123 A1 | 8/2007 | Houzego |
| 2007/0194041 A1 | 8/2007 | Stradella |
| 2007/0210102 A1 | 9/2007 | Stradella |
| 2007/0241136 A1 | 10/2007 | Poulard |
| 2007/0246042 A1 | 10/2007 | Purkins et al. |
| 2007/0251950 A1 | 11/2007 | Bacon |
| 2007/0284383 A1 | 12/2007 | Wright |
| 2008/0017189 A1 | 1/2008 | Ruckdeschel et al. |
| 2008/0017193 A1 | 1/2008 | Jones et al. |
| 2008/0035144 A1 | 2/2008 | Bowman et al. |
| 2008/0041877 A1 | 2/2008 | Stradella et al. |
| 2008/0047556 A1 | 2/2008 | Hodson |
| 2008/0060643 A1 | 3/2008 | Hodson et al. |
| 2008/0066742 A1 | 3/2008 | Hodson et al. |
| 2008/0092887 A1 | 4/2008 | Hodson et al. |
| 2008/0115784 A1 | 5/2008 | Gumaste et al. |
| 2008/0135575 A1 | 6/2008 | Ingram et al. |
| 2008/0135576 A1 | 6/2008 | Bacon |
| 2008/0173301 A1 | 7/2008 | Deaton et al. |
| 2008/0210224 A1 | 9/2008 | Brunnberg et al. |
| 2008/0210226 A1 | 9/2008 | Butterworth et al. |
| 2008/0251004 A1 | 10/2008 | Stradella et al. |
| 2008/0283541 A1 | 11/2008 | Warby et al. |
| 2008/0314383 A1 | 12/2008 | Barney et al. |
| 2009/0114219 A1 | 5/2009 | Ferris et al. |
| 2009/0211578 A1 | 8/2009 | Fletcher |
| 2009/0229604 A1 | 9/2009 | Pearson et al. |
| 2009/0229607 A1 | 9/2009 | Brunnberg et al. |
| 2009/0293870 A1 | 12/2009 | Brunnberg et al. |
| 2009/0308385 A1 | 12/2009 | Brewer et al. |
| 2009/0308389 A1 | 12/2009 | Pocock et al. |
| 2010/0012115 A1 | 1/2010 | Bacon |
| 2010/0065050 A1 | 3/2010 | Holroyd |
| 2011/0311138 A1* | 12/2011 | Williams et al. .............. 382/173 |
| 2012/0017900 A1 | 1/2012 | Bacon |
| 2012/0020002 A1* | 1/2012 | Mathew et al. .......... 361/679.27 |

FOREIGN PATENT DOCUMENTS

| | | |
|---|---|---|
| AU | 2003234746 | 9/2003 |
| AU | 2003234748 | 9/2003 |
| DE | 4111895 | 10/1992 |
| DE | 19745513 | 4/1999 |
| DE | 29818662 U | 3/2000 |
| DE | 10061723 C | 7/2002 |
| EP | 0428380 B | 5/1991 |
| EP | 0501365 | 9/1992 |
| EP | 0629563 A | 12/1994 |
| EP | 1 201 423 | 5/2002 |
| EP | A-1201423 | 5/2002 |
| EP | A-0820322 | 5/2004 |
| EP | 1 169 245 | 8/2006 |
| FR | 2654627 | 5/1991 |
| FR | 2660630 | 10/1991 |
| FR | 2701653 | 8/1994 |
| GB | 161969 | 7/1922 |

| | | |
|---|---|---|
| GB | 2385640 | 9/1945 |
| GB | 939324 | 10/1963 |
| GB | 1 026 763 | 4/1966 |
| GB | 1026763 | 4/1966 |
| GB | A-1 026 763 | 4/1966 |
| GB | 1270272 | 4/1972 |
| GB | 2195544 | 4/1988 |
| GB | 2262452 A | 6/1993 |
| GB | 2263873 | 8/1993 |
| GB | 2264238 A | 8/1993 |
| GB | 2266466 A | 11/1993 |
| GB | 2278979 B | 1/1995 |
| GB | 2279571 A | 1/1995 |
| GB | 2292891 A | 3/1996 |
| GB | 2 279 879 B | 10/1997 |
| GB | 2 348 928 | 10/2000 |
| GB | 2366519 B | 3/2002 |
| GB | 2 372 543 | 8/2002 |
| GB | 2 372 542 | 8/2003 |
| GB | 2398250 A | 8/2004 |
| GB | 2398251 A | 8/2004 |
| GB | 2 381 201 | 2/2005 |
| GB | 2429166 A | 2/2007 |
| JP | 56-155759 | 12/1981 |
| JP | 57-75855 | 5/1982 |
| JP | 63251880 | 10/1988 |
| JP | 2003-056254 | 2/2003 |
| WO | WO 92/07599 | 5/1992 |
| WO | WO 92/07600 | 5/1992 |
| WO | WO 93/03783 | 3/1993 |
| WO | WO 93/24167 | 12/1993 |
| WO | WO 94/05359 | 3/1994 |
| WO | WO 94/19042 | 9/1994 |
| WO | WO 95/08484 | 3/1995 |
| WO | WO 96/39337 | 12/1996 |
| WO | WO 97/11296 | 3/1997 |
| WO | WO 97/30743 A2 | 8/1997 |
| WO | WO 98/01822 | 1/1998 |
| WO | WO 99/06091 | 2/1999 |
| WO | WO 99/06092 | 2/1999 |
| WO | WO 99/36116 | 7/1999 |
| WO | WO 01/31578 | 5/2001 |
| WO | WO 01/34231 A1 | 5/2001 |
| WO | WO 01/37909 | 5/2001 |
| WO | WO 02/16235 | 2/2002 |
| WO | 02/24552 | 3/2002 |
| WO | WO 02/24552 | 3/2002 |
| WO | WO 02/38207 | 5/2002 |
| WO | WO 02/43794 | 6/2002 |
| WO | WO 03/035155 A1 | 5/2003 |
| WO | WO 03/080161 | 10/2003 |
| WO | WO 2004/073776 | 9/2004 |
| WO | WO 2004/089451 | 10/2004 |
| WO | WO 2004/096329 | 11/2004 |
| WO | WO 2006/054083 | 5/2006 |
| WO | WO 2006/062449 | 6/2006 |
| WO | WO 2006/119766 | 11/2006 |
| WO | WO 2007/012854 | 2/2007 |
| WO | WO 2007/022898 | 3/2007 |
| WO | WO 2007/029019 | 3/2007 |
| WO | WO 2007/034237 | 3/2007 |
| WO | WO 2007/066140 | 6/2007 |
| WO | WO 2007/077450 | 7/2007 |
| WO | WO 2007/103712 | 9/2007 |
| WO | WO 2007/107431 | 9/2007 |
| WO | WO 2007/141520 | 12/2007 |
| WO | WO 2008/025087 | 3/2008 |
| WO | WO 2008/040772 | 4/2008 |
| WO | WO 2008/079350 | 7/2008 |
| WO | WO 2008/079360 | 7/2008 |
| WO | WO 2008/087369 | 7/2008 |
| WO | WO 2008/104366 | 9/2008 |
| WO | WO 2008/119552 | 10/2008 |
| WO | WO 2008/148864 | 12/2008 |

OTHER PUBLICATIONS

Japanese Office Action dated Sep. 24, 2010, issued in corresponding Japanese Application No. 2007-547614 (in English)—6 pages.
"Polyethylene—linear low density (LLDPE) CAS No. 9002-88-4" http://www.icis.com/v2/chemicals/9076159/polyethylene-linear.low.density.html. (Jan. 19, 2011).
Rejection Decision from copending Japanese Application citing JP 57-75855 and JP 56-155759 (one page).
Rejection Decision dated Feb. 25, 2011, from copending Japanese Application No. 2007-547614, citing JP 57-75855 and JP 56-155759 (one page).
U.S. Appl. No. 13/138,591, filed Jan. 2012, Bacon et al.
International Search Report for PCT/GB201 0/050405, mailed Jun. 16, 2010.
Written Opinion of the International Searching Authority for PCT/GB2010/050405 mailed Jun. 16, 2010.

* cited by examiner

MEDICAMENT CONTAINER

This application is the US national phase of international application PCT/GB2005/004834 filed 14 Dec. 2005, which designated the U.S. and claims benefit of GB 0428204.2, filed 23 Dec. 2004, the entire contents of each of which are hereby incorporated by reference.

The present invention relates to a container for a medicament, particularly of not exclusively for use in a pressurised source of a medicament.

Sources of medicament having metered dose release valves conventionally are provided with aluminium containers of the medicament. As such, the user cannot see the amount of medicament left.

Expensive counters for counting the number of operations of the valve are coming to be provided to enable the user to assess the number of doses remaining.

The object of the present invention is to provide an alternative means of providing this assessment, namely visually.

According to a first aspect of the invention there is provided a container for a medicament in a medicament source, the container having:
a mouth with a rim for a closure of the medicament source, the container including a plurality of layers of polymeric material, the layers comprising at least:
  an inner, substance-repellent layer;
  an outer gas-tight and liquid-impermeable layer,
the two layers being of transparent or at least translucent material.

According to a second aspect of the invention there is provided a container for a medicament in a medicament source, the container having:
a mouth with a rim for a closure of the medicament source, the container including a plurality of layers of polymeric material, the layers comprising at least:
  an inner, substance-repellent layer;
  a second, gas-tight layer; and
  a third, liquid-impermeable layer,
the three layers being of transparent or at least translucent material.

The gas tight layer can be inside the liquid-impermeable layer or outside it.

Whilst other forms of closure can be envisaged, in particular welded closures, the usual closure is expected to be a crimp closure.

The inner layer is provided to avoid wetting of the inside surface of the container by the medicament or adsorption of it by the container's material. Suitably, polytetrafluoroethylene can be used for the inner layer.

The second gas-tight layer is provided to retain the medicament against permeation through the container under pressure and also to retain a propellant, within the container, where as is normally the case, the container is being used in a pressurised source of the medicament. Suitably, nylon can be used for the second layer.

The third layer is provided to retain the liquid carrier of the medicament, which will normally be water. Suitably, polypropylene can be used for the third layer. An further purpose of the third layer is to stop ingress of water from without the container, in particular where the medicament can degrade in the presence of water A reinforcing layer may be provided. This may be a perforate metallic layer or a fibre reinforcement. The reinforcing layer may be added after moulding formation of the container or may be incorporated into the container during moulding.

The reinforcing layer will normally be perforate, open weave textile or possibly spirally wound, in order that the level of the medicament within the container can be assessed.

According to a third aspect of the invention, there is provided a method of producing the container of the first aspect, the method consisting in the steps of
injection moulding a laminated preform and
blowing the preform to finished shape.

The reinforcing layer can be included in the blowing mould prior to blowing of the preform to shape to suit.

To help understanding of the invention, a specific embodiment thereof will now be described by way of example and with reference to the accompanying drawings, in which.

Figure 4:
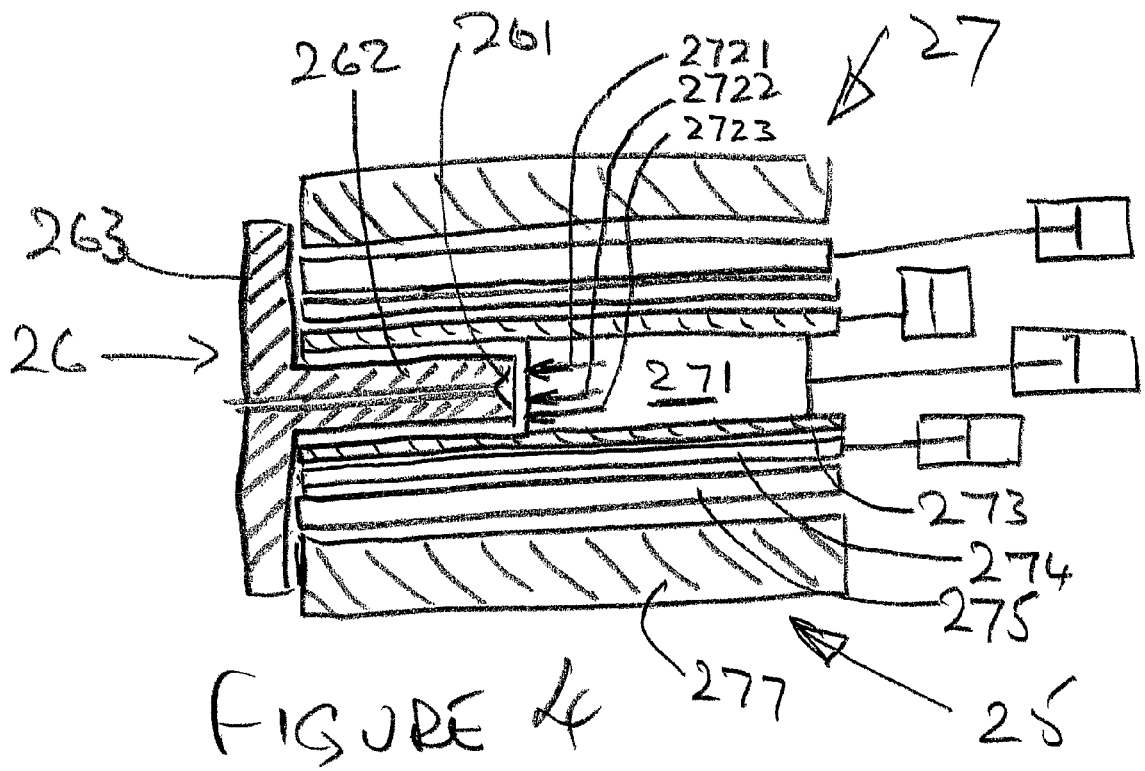
Figure 5:
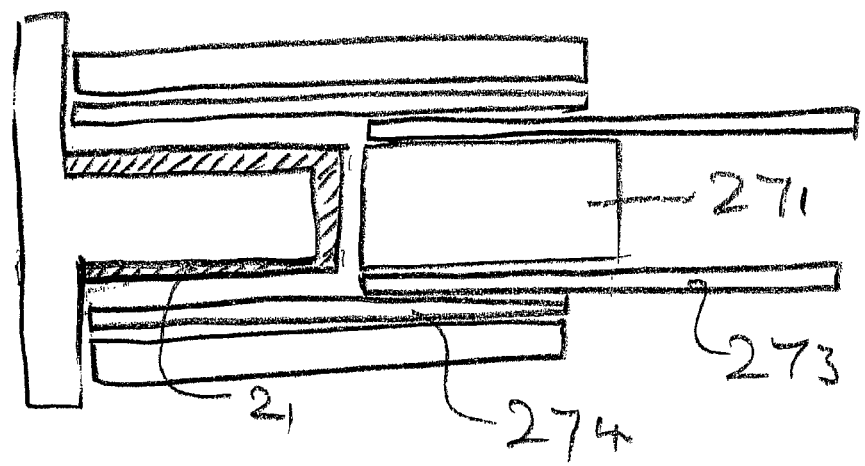
Figure 6:
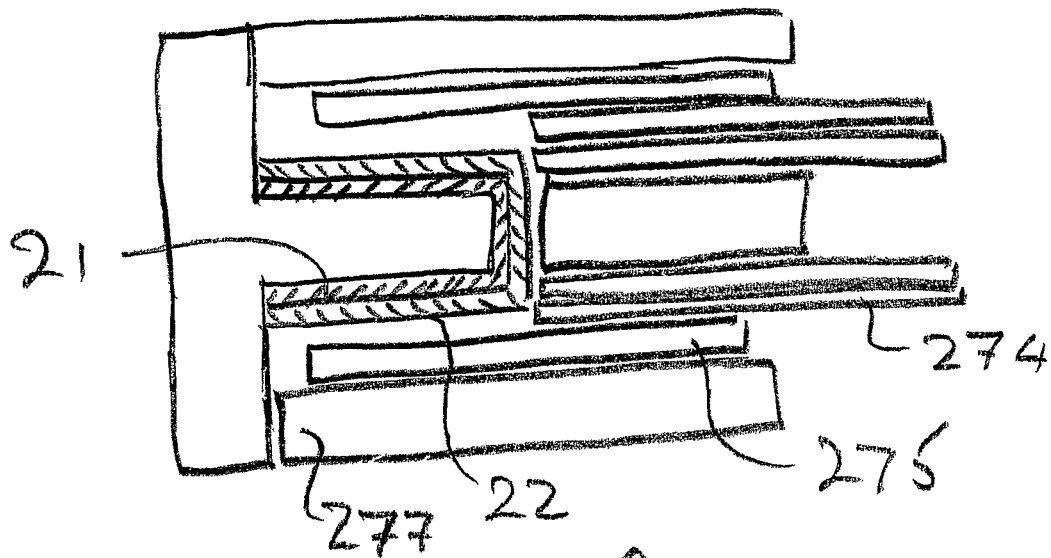
Figure 7:
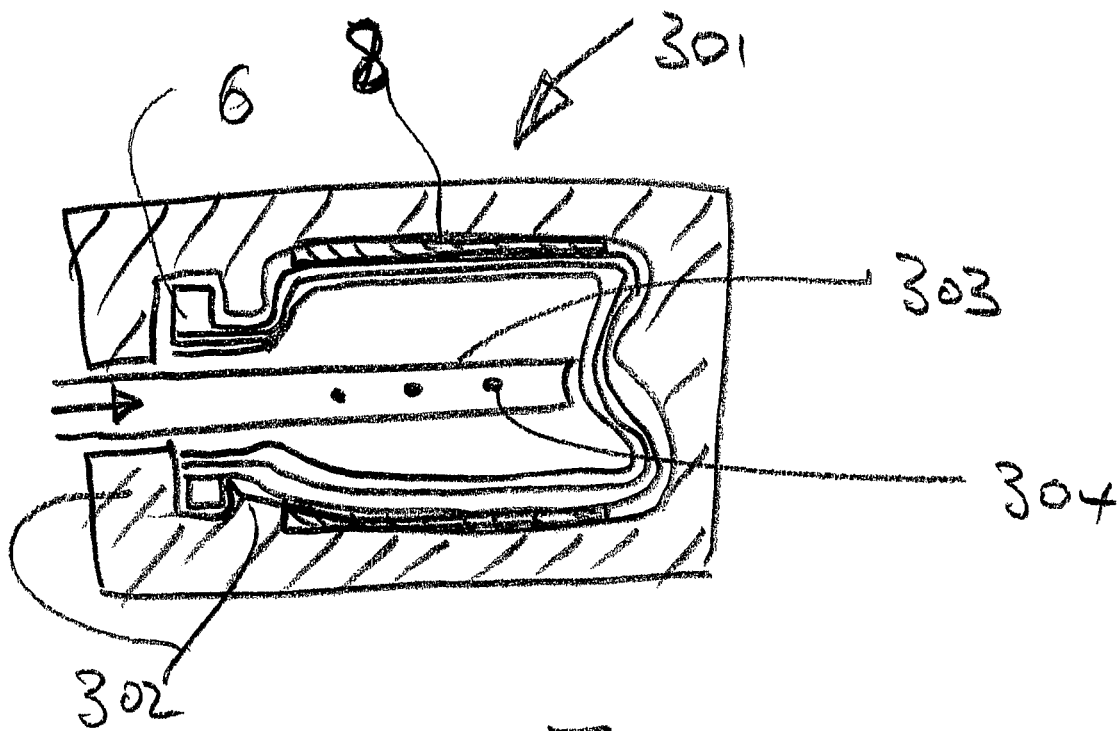

FIG. 4 longitudinal cross-sectional view of an injection moulding tool configured for injection of the inner layer of the container;

FIG. 5 is a similar view of the too 1 configured for injection of the second layer;

FIG. 6 is a third view of the tool configured for injection of the third layer; and FIG. 7 is a similar view of the injection moulded preform blown to size in a blow moulding cavity.

Figure 1:
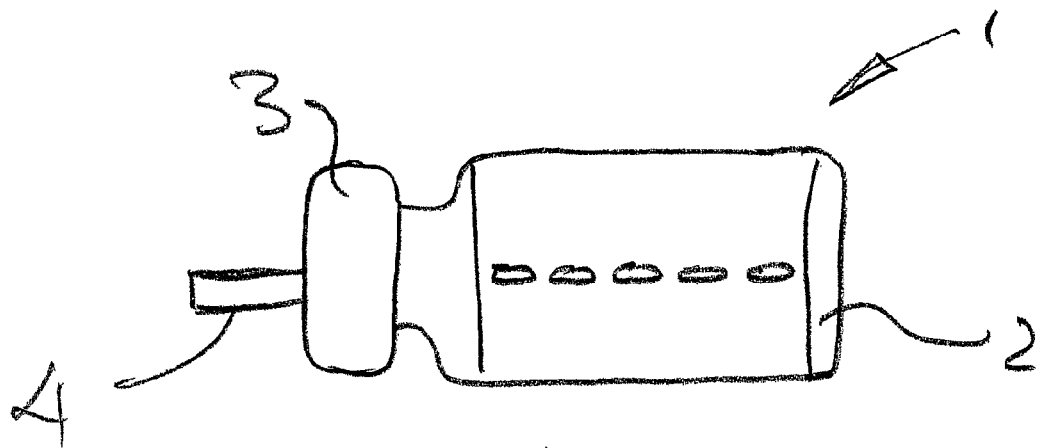
FIG. 1 is a side view of a metered-dose, source of a medicament, the source including a container according to the invention.

Referring to the drawings, the medicament source 1 of FIG. 1 has a container 2 of the invention and a crimped closure 3. The closure sealingly holds to the container a metered-dose release valve, of which the spout 4 only is visible in FIG. 1.

Figure 2:
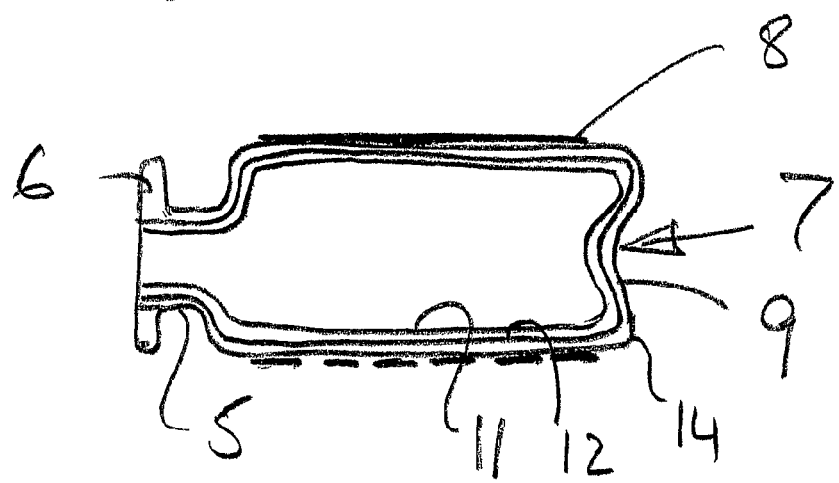
FIG. 2 is a similar cross-sectional side view of the container of the source of FIG. 1.

As shown in FIG. 2, the container has a neck 5 and a protruding rim 6 at which the crimp locates. The container is of moulded polymer 7 and has an outer, perforate sleeve 8 of aluminium sleeve, providing mechanical strength for pressure retention. The neck has a relatively thicker wall thickness of polymer, enabling pressure retention and the polymer end 9 is domed inwards, also for pressure retention.

The polymer is of three layers or laminations. The innermost layer 11 is of polytetrafluoroethylene (PTFE) material. This is provided as an inert layer with which the medicament and its propellant will not react or combine in any way. The middle polymer layer is of nylon material. This is provided as a propellant tight layer 12, to contain the propellant, whose molecules may be able to pass through the PTFE layer. The outer polymer layer 14 is of polypropylene (PP). It is thicker than the other two layers to provide both water tightness and mechanical integrity of the container. The three polymer layers are in intimate contact with each other and the PP layer is in intimate contact with the aluminium.

Figure 3:
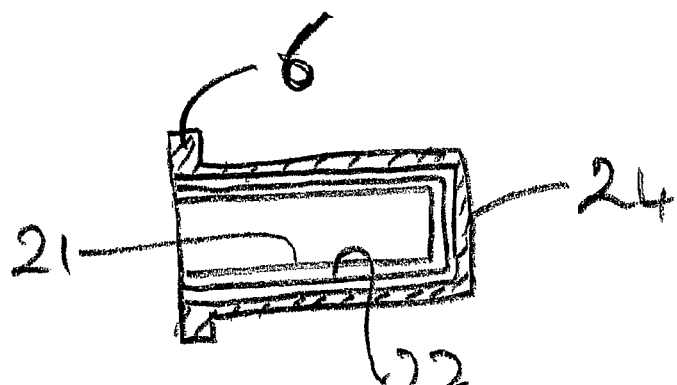
FIG. 3 is a similar view of a preform for the container of FIG. 2.

Referring now to FIGS. 3 and 4, the container 2 is formed as a blow moulding from the preform shown in FIG. 3, the preform being injection moulded in the tool shown in FIG. 4. The preform is a shorter, squatter configuration of the container, and as such will not be separately described, save to say that its layers are designated as follows:
inner PTFE layer 21
middle nylon layer 22
outer PP layer 24.

The operative parts only of the mould tool 25 are shown and comprise a male part 26 and a female part 27. The male part is conventional in having no moving parts, except for an expulsion air tappet valve 261 mounted in a male core part 262, the latter being integral with a backing plate 263. The female part on the other hand has several moving parts, including a central gate part 271, with three gates 2721 for PTFE, 2722 for nylon and 2723 for PP. The gate part is movable by the respective thickness of the layers 22 and 24, in other words for injection and moulding of the PTFE layer the central part is advanced towards the male core part 262 and spaced from it by the thickness of the PTFE layer. Then for injection of the nylon layer, the central part is withdrawn by the thickness of the nylon part and for injection of the PP layer it further withdrawn by the thickness of the PP layer. The mechanical and hydraulic details of the design of the central part and the mould tool in general are expected to be within the capabilities of the skilled man and as such will not be described in more detail.

Coaxial with the male core part 262 and the female gate part 271 are three sleeves 273, 274, 275, all individually and selectively withdrawable away from the male backing plate 263. The first sleeve is in its advanced position shown in FIG. 4 for moulding of the PTFE layer 21. This is moulded in the cavity formed between the male core part, the female gate part and the sleeve 273. For moulding of the nylon layer, the sleeve 273 is withdrawn as is the gate part 271 to its first withdrawn position. A mould cavity now exists between the PTFE layer 21, sleeve 274 and the gate part and the nylon layer is injected into this, see FIG. 5.

Both the PTFE and nylon layers are circular cylindrical, open at one end and closed at the other. The PP layer is similar saving having the shoulder or rim 6. To form this, not only is the sleeve 274 withdrawn, but also the outer sleeve 275 is partially withdrawn. Thus the mould cavity is formed to a shape suitable for moulding the PP layer complete with its shoulder, see FIG. 6. The circumference of the shoulder is formed against a fixed part 277 of the female mould part.

The resultant moulding is ejected from the injection moulding tool and transferred to the blow moulding tool 301, shown in FIG. 7. This a largely conventional tool, save that it is provided with a reinforcing sleeve 8 prior to insert of the preform. This is gripped at it shoulder 6 by mould features 302 and stretched by a rod 303 to its full use length. Gas is injected into the preform via drillings 304 in the rod and the preform is blown to its full diameter, in which the PP layer comes into intimate contact with the aluminium sleeve.

The invention is not intended to be restricted to the details of the above described embodiment. For instance, other polymers having like properties respectively to PTFE, nylon and PP may be used. Again other reinforcements such as fibre reinforcement can be used. Further it is envisaged that no reinforcement may be necessary. Again other processes than preform and blow moulding may be used for making containers of the invention.

Further, the invention is equally as applicable to non-metered dose pressurised sources of a medicament using a container of the invention as metered dose sources.

The invention claimed is:

1. A container comprising a pressurised medicament for use in a medicament source,
the container comprising a mouth with a rim for a closure of the medicament source, and
the container comprising a plurality of layers comprising:
a first, inner, substance-repellent layer to repel the medicament;
a second gas-tight layer; and
a third, liquid-impermeable layer;
wherein said layers are of a polymeric material and
said layers are of transparent or translucent material, and
the container comprising the pressurised medicament comprises a pressurised propellant and a reinforcing layer including fibre reinforcement to retain the pressure of the pressurised medicament.

2. A container as claimed in claim 1, wherein the gas tight layer is inside the liquid-impermeable layer.

3. A container as claimed in claim 1, wherein the gas tight layer is outside the liquid-impermeable layer.

4. A container comprising a pressurised medicament for use in a medicament source,
the container comprising a mouth with a rim for a closure of the medicament source, and
the container comprising a plurality of layers comprising:
an inner, substance-repellent layer to repel the medicament; and
an outer gas-tight and liquid-impermeable layer;
wherein said layers are of polymeric material and
said layers are of transparent or translucent material and
the container comprising the pressurised medicament comprises a pressurised propellant and a reinforcing layer including fibre reinforcement to retain the pressure of the pressurised medicament.

5. A container as claimed in claim 4 or claim 1, including a welded closure or a crimp closure.

6. A container as claimed in claim 4 or claim 1, wherein the container is moulded and the reinforcing layer is incorporated in a post-moulding addition to the container.

7. A container as claimed in claim 4 or claim 1, wherein the reinforcing layer is incorporated into the container as moulded.

8. A container as claimed in claim 4 or claim 1, wherein the reinforcing layer is perforate, of open weave textile or spirally wound for visual assessment of the level of the medicament within the container.

9. A container as claimed in claim 4 or claim 1, wherein said inner layer comprises polytetrafluoroethylene.

10. A container as claimed in claim 4 or claim 1, wherein said gas-tight layer comprises nylon.

11. A container as claimed in claim 4 or 1, wherein the reinforcing layer includes a pressure retaining sleeve surrounding said plurality of polymeric layers.

12. The container of claim 11 wherein said sleeve is perforated.

13. The container of claim 12 wherein said sleeve is aluminium.

14. A method of moulding a container as claimed in claim 4 or claim 1, the method consisting in the steps of:
injection moulding a laminated preform,
including a reinforcing layer including fibre reinforcement in a blowing mould, and
blowing the preform to finished shape in the mould.

\* \* \* \* \*